United States Patent

Blankenstein et al.

[11] Patent Number: 5,447,898
[45] Date of Patent: * Sep. 5, 1995

[54] PROCESS FOR THE PREPARATION OF ZIRCONIA

[75] Inventors: Paul Blankenstein; Paulus J. M. Rek, both of Amsterdam, Netherlands

[73] Assignee: Shell Oil Company, Houston, Italy

[*] Notice: The portion of the term of this patent subsequent to Oct. 8, 2010 has been disclaimed.

[21] Appl. No.: 306,039

[22] Filed: Sep. 14, 1994

[30] Foreign Application Priority Data

Sep. 21, 1993 [EP] European Pat. Off. ............ 93202731

[51] Int. Cl.$^6$ .............................................. B01J 21/06
[52] U.S. Cl. ..................................... 502/349; 423/608
[58] Field of Search .......................... 502/349; 423/608

[56] References Cited

U.S. PATENT DOCUMENTS

| | | | |
|---|---|---|---|
| 2,442,772 | 6/1948 | Marisic et al. | 196/52 |
| 2,467,089 | 4/1949 | Marisic et al. | 23/140 |
| 4,822,575 | 4/1989 | Ngian et al. | 423/82 |
| 5,217,938 | 6/1993 | Reinalda et al. | 502/325 |

FOREIGN PATENT DOCUMENTS

0510772A1 10/1992 European Pat. Off. .
2590887A 12/1985 France .

OTHER PUBLICATIONS

Kirk-Othmer, Encyclopedia of Chemical Technology, 2n Ed., vol. 22, pp. 651-655.
P. D. L. Mercera et al., "Zirconia as a Support For Catalysts: Evolution of the Texture & Structure on Calcination in Air", Appl. Catalysis 57 (1990) pp. 127-148.
B. H. Davis et al., "Catalytic Conversion of Alcohols II. Influence of Preparation and Pretreatment on the Selectivity of Zirconia", Ind. Eng. Chem. Prod. Res. Dv., vol 18, No. 3, 1979 pp. 191-198.
M. J. Torralvo et al., "Crystallization Behaviour of Zirconium Oxide Gels", Journal of Catalysis 86(1984) pp. 473 to 476.

Primary Examiner—Anthony McFarlane

[57] ABSTRACT

A process for the preparation of a zirconia precursor comprises contacting a solution of an acidic zirconium compound with a solution of a basic zirconium compound to form a gel. A shapable dough may be formed by rendering the zirconia precursor shapable, for example by drying the zirconia precursor or combining the zirconia precursor with a solid filler. The shapable dough may be shaped, for example by extrusion, to form a shaped zirconia precursor, which in turn may be dried and calcined to form shaped zirconia particles. The shapable dough may be prepared so as to comprise a source for a catalytically active component, in which case the shaped zirconia particles may be used directly as a catalyst. A source of a catalytically active component may be deposited on the shaped zirconia particles to yield a finished catalyst.

12 Claims, No Drawings

PROCESS FOR THE PREPARATION OF ZIRCONIA

FIELD OF THE INVENTION

The present invention relates to a process for the preparation of a zirconia precursor, a shapable dough and shaped zirconia particles, in particular to a zirconia precursor, a shapable dough and shaped zirconia particles useful in the preparation of a catalyst or catalyst precursor.

BACKGROUND OF THE INVENTION

Zirconia (zirconium dioxide) finds use as a catalyst or as a carrier or support material for a catalyst. When being used either as a catalyst or a catalyst carrier, it is desirable that the zirconia has a high surface area and that the surface area is stable at high temperatures. Further, to be suitable for use as a catalyst or catalyst carrier in many applications, it is also important that the zirconia product has sufficient strength for the required application. This is particularly the case when the catalyst comprises particles of zirconia which have been shaped, for example by extrusion.

Zirconia exists in a number of crystalline forms, dependant upon the prevailing conditions. Thus, zirconia exists under ambient conditions of temperature and pressure as a stable, monoclinic crystalline structure. Under extreme pressures or at higher temperatures, typically of the order of 450° to 1000° C., zirconia exists as a tetragonal crystalline structure. At even higher temperatures, typically in excess of 1500° C., a cubic crystalline phase forms. For a general discussion of the properties of zirconia, reference is made to Kirk-Othmer "Encyclopedia of Chemical Technology", Second Edition, Volume 22, pages 651 to 655.

The preparation of zirconia may be achieved by methods well known in the art. Thus, French patent application publication No. 2 590 887 (FR-A-2 590 887) discloses the preparation of zirconia by a method comprising precipitating zirconium hydroxide from a solution of zirconyl nitrate by the addition of aqueous ammonia solution, followed by drying and calcining the resulting precipitate. Similar methods are disclosed by B. H. Davis et al "Catalytic Conversion of Alcohols. II. Influence of Preparation and Pretreatment on the Selectivity of Zirconia", Ind Eng Chem Prod Res Dev., vol 18, No 3, 1979, pages 191 to 198, and M. J. Torralvo et al, "Crystallisation Behaviour of Zirconium Oxide Gels", Journal of Catalysis 86 (1984), pages 473 to 476. U.S. Pat. No. 4,822,575 discloses a similar method in which zirconia is prepared by the calcination of the precipitate formed upon the addition of ammonia to an aqueous solution of zirconium sulphate.

P. D. L. Mercera et al, "Zirconia as a Support for Catalysts: Evolution of the Texture and Structure on Calcination in Air", Applied Catalysis, 57 (1990) pages 127 to 148, describe the preparation of zirconia samples by precipitation from a solution of zirconyl chloride at a pH of 10, followed by calcination in air at temperatures of up to 850° C. This gel-precipitation technique yielded zirconia having a high surface area (up to 111 $m^2/g$ measured by BET after calcination at 450° C). The zirconia had a well developed mesoporous structure. However, P. D. L. Mercera et al report that the porous texture was unstable, with the initial high surface area being lost rapidly with increasing calcination temperature. The gel prepared during the experiments crystallized upon calcination into the tetragonal structure. However, P. D. L. Mercera found that, upon cooling, the zirconia underwent a phase transformation, yielding a substantially monoclinic crystalline product, resulting in a loss of surface area and pore volume. This in turn resulted in shrinkage of the zirconia structure and a reduction in the material's strength.

A number of methods have been proposed for preparing stable, high surface area zirconia. Thus, USSR patent number 1 370 079 (SU-A-1 370 079) discloses a process for the preparation of monoclinic zirconia comprising the reaction of an aqueous ammonia solution with an aqueous solution of zirconium nitrate, washing and drying the gel so-obtained, and then subjecting the product to a heat treatment in which it is held at a temperature of from 150° to 175° C. under a pressure of 6 to 10 atmospheres in the presence of steam for 2 to 10 hours. It is stated in SU-A-1 370 079 that the process yields zirconia free from tetragonal crystalline phase, having a high specific surface area of 105 $m^2/g$ and a pore volume of 0.19 ml/g.

Further, FR-A-2 590 887 referred to hereinbefore discloses a composition comprising zirconia in combination with an additive selected from an oxide of silicon, a rare earth metal or aluminum. The additive is said to stabilize the specific surface area of the zirconia at high temperatures. Preferred stabilizing additives are yttrium, lanthanum and cerium. The additive may be present in the composition in an amount of from 1 to 10% by weight, preferably from 2 to 5% by weight. The composition may be prepared by the co-precipitation of a precursor of the additive compound and a precursor of zirconia. Alternatively, the additive may be incorporated into the composition by the impregnation of a zirconia material.

U.S. Pat. Nos. 2,442,772 and 2,467,089 (US-A-2,442,772 and US-A-2,467,089, respectively) both disclose a method for the preparation of stable zirconia hydrogels. The method comprises reacting an aqueous solution of a soluble zirconium compound with water soluble salts of at least two weak acids, such as acetic acid, carbonic acid and nitrous acid, to yield homogeneous zirconia hydrosols containing substantially no precipitate. US-A-2,442,772 and US-A-2,467,089 describe using the product as such as a catalyst or catalyst component. Alternatively, the product may be impregnated with other oxides or the like or milled with other materials. The milling may be carried out with the hydrogel in a wet form, optionally with wet silica gel, in a ball mill, prior to extrusion.

As mentioned hereinbefore, many catalytic applications employ preshaped catalyst particles, shaped using such techniques as extrusion and pelletizing. European patent application publication No. 0 510 772 (EP-A-0 510 772) discloses a process for the preparation of a zirconia-based catalyst or catalyst precursor comprising mulling a mixture of zirconia and/or a zirconia precursor and a solvent, which mixture has a solids content of from 20 to 60% by weight, and extruding the mixture. The resulting extrudates may be impregnated with a suitable catalytically active element, preferably cobalt.

It has been found that zirconia extrudates prepared using the method described in EP-A-0 510 772 can suffer shrinkage upon calcination, leading to weaker extrudates which may not meet the specifications of strength necessary for some applications. In such cases, a refractory oxide, such as silica, may be added to the mixture being extruded to act as a binder and improve the strength of the final calcined extrudates.

It has now been found that a zirconia precursor most suitable for preparing zirconia-containing catalysts or catalyst precursors may be prepared by contacting a solution of an acidic zirconium compound with a solution of a basic zirconium compound, yielding the precursor in the form of a material hereafter referred to as a "gel".

SUMMARY OF THE INVENTION

Accordingly, the present invention provides a process for the preparation of a zirconia precursor, which process comprises contacting a solution of an acidic zirconium compound with a solution of a basic zirconium compound to form a gel. The present invention also provides a zirconia precursor obtainable by the process hereinbefore described.

DESCRIPTION OF THE PREFERRED EMBODIMENTS

Suitable acidic zirconium compounds for use in the process include both organic and inorganic acid salts of zirconium. Suitable inorganic salts are, for example, zirconyl chloride, zirconyl nitrate, zirconium chloride and zirconium phosphate. Suitable organic salts include zirconium acetate, zirconium ethanoate and zirconium propanoate. Particularly suitable acidic zirconium compounds are the organic acid salts, especially zirconium acetate.

Suitable basic zirconium compounds for use in the process include both organic and inorganic zirconium compounds. Suitable basic compounds include zirconium carbonate and basic zirconium complexes. A most suitable basic zirconium compound is ammonium zirconium carbonate.

The acidic and basic zirconium compounds are each dissolved in a suitable solvent to form a solution. Preferably, the same solvent used to form both solutions. The solvent may be any of the suitable solvents known in the art, for example water; alcohols, such as methanol, ethanol and propanol; ketones, such as acetone; aldehydes, such as propanal; and aromatic solvents, such as toluene. A most convenient and preferred solvent is water.

The two solutions may be contacted very simply by mixing. The zirconia precursor, in the form of the gel, may be recovered from the combined solutions by filtration. The zirconia precursor is preferably washed to remove traces of the original acidic and basic solutions.

The zirconia precursor prepared in this manner is most suitable as a starting material in the preparation of shaped zirconia particles for use as catalysts or catalyst precursors. As a first step in this process, the zirconia precursor is formed into a shapable material, hereafter referred to as a "shapable dough".

In a second aspect, the present invention provides a process for the preparation of a shapable dough suitable for use in the preparation of a shaped zirconia precursor, which process comprises rendering shapable the zirconia precursor prepared as hereinbefore described. The present invention also provides the shapable dough obtainable by such a process.

The shapable dough is prepared from the zirconia precursor by decreasing the ratio of solvent present in the zirconia precursor to the solid content of the zirconia precursor. This may be achieved by drying the zirconia precursor, that is reducing the solvent content of the zirconia precursor. As an alternative to drying, the shapable dough may be obtained by combining the zirconia precursor with a solid filler. A combination of drying and addition of a solid filler may be applied to prepare the shapable dough.

Suitable techniques for drying the zirconia precursor are well known in the art. Typically, drying may be achieved by heating the zirconia precursor to a temperature of up to about 200° C., more preferably up to about 150° C. The temperature is selected so as to be high enough to evaporate the solvent from the zirconia precursor, without effecting a substantial chemical change to the zirconia precursor.

Suitable fillers for addition to the zirconia precursor include the refractory oxides, such as alumina, silica, titania and zirconia. Silica is a most suitable filler for use in the formation of the shapable dough.

The shapable dough is prepared so as to have the solids content necessary for the shaping process to be applied. Typically, the solids content of the shapable dough will be in the range of from 20 to 60% by weight, more preferably from 20 to 50% by weight.

The preparation of the shapable dough from the zirconia precursor preferably comprises a mulling operation. The use of a mulling operation allows the optimum texture of the shapable dough to be obtained in preparation for a subsequent shaping stage. This is particularly advantageous when a filler is used to prepare the shapable dough.

In addition, to improve the flux properties of the dough to be shaped, the dough may comprise one or more surface active agents or polyelectrolytes, often referred to as flow improvers. The flow improvers may conveniently be included in the composition during the mulling operation. The addition of a flow improver results in a smoother texture and facilitates in the subsequent shaping operation. Suitable flow improvers include fatty amines, quaternary ammonium compounds, aliphatic monocarboxylic acids, ethoxylated alkyl amines, polyvinyl pyridine and sulfoxonium, sulfonium, phosophonium and iodonium compounds, alkylated aromatic compounds, acyclic monocarboxylic acids, fatty acids, sulphonated aromatic compounds, alcohol sulfates, ether alcohol sulfates, sulfated fats and oils and phosphonic acid salts, polyethylene alkylphenols, polyoxyethylene alcohols, polyoxyethylene alkylamines, polyoxyethylene alkylamides, polyols and acetylenic glycols. Preferred additives are sold under the trademarks Nalco and Superfloc.

The flow improvers are preferably present in the shapable dough in a total amount in the range of from 1 to 20% by weight, more preferably from 2 to 10% by weight, on the basis of the total weight of the mixture.

Typically, the shapable dough is mulled for a total period of from about 10 to about 120 minutes, preferably from 15 to 90 minutes. During the mulling process, energy is input into the dough by the mulling apparatus. The rate of energy input into the dough is typically in the range of from 0.05 to 50 Wh/min/kg, preferably from 0.5 to 10 Wh/min/kg. The mulling process may be carried out at a broad range of temperature, preferably from 15° to 50° C. As a result of the energy input into the dough during the mulling process, there will be a rise in temperature of the dough during the mulling. The mulling process is conveniently carried out at ambient pressure. Any suitable, commercially available mulling machine may be employed.

If desired, the shapable dough may be prepared so as to comprise a source for one or more catalytically active components. For the purposes of this specification, the term "catalytically active component" is a reference to elements active as catalysts with respect to one or more reactions, as well as elements active as co-catalysts or promoters. Accordingly, the dough may comprise a source for one or more elements selected from Groups IB, IIB, IIIB, IVB, VB, VIB, VIIB, VIII of the Periodic Table of Elements, or the Lanthanides and Actinides. In particular, the dough may comprise a source for one or more elements in Group VIII of the Periodic Table, in particular elements selected from iron, ruthenium, cobalt, rhenium, nickel, palladium and platinum, especially cobalt, iron and nickel, or elements from Group IVB of the Periodic Table, in particular titanium and/or zirconium.

Typical sources for catalytically active components include salts derived from organic acids, for example acetates, benzoates, ethanoates and propanoates; halides, for example chlorides, bromides, iodides and fluorides; and other salts, for example nitrates, oxides, hydroxides, carbonates and chlorates. The source of the catalytically active component may be included in the dough during the mulling operation.

As mentioned hereinbefore, the shapable dough is a most suitable starting material for the preparation of shaped zirconia particles, referred to in this specification as "a shaped zirconia precursor". Accordingly, in a further aspect, the present invention provides a process for the preparation of a shaped zirconia precursor, which process comprises shaping a dough as hereinbefore described. The present invention also provides a shaped zirconia precursor obtainable by such a process.

Any suitable shaping technique known in the art may be applied in the shaping of the dough of this invention. One suitable technique for shaping the dough is pelletizing. A most suitable shaping process, in particular suited to the preparation of shaped catalyst precursors is extrusion. Extrusion may be effected using any conventional, commercially available extruder. In particular, a screw-type extruding machine may be used to force the dough through orifices in a suitable dieplate to yield extrudates of the desired form. The strands formed upon extrusion may be cut or broken to the desired length.

The extrudates may have any suitable form. Examples of commonly applied forms include cylinders, for example solid or hollow cylinders. Alternatively, the extrudates may be multilobed or twisted multilobed in cross section. For catalytic applications, extrudates typically have a nominal diameter in the range of from 0.5 to 5 mm, more preferably from 1 to 3 mm.

It is a feature of the process and products of the present invention that it is not necessary to peptize either the shapable dough or the filler during the shaping process. This has been found to be unnecessary. By way of comparison, in the process described and exemplified in EP-A-0 510 772 it is a preferred feature that the mixture is first treated using a peptizing agent prior to extrusion. In the Example of EP-A-0 510 772, this has the effect of peptizing both the silica and the zirconia present in the mixture. This in turn has the effect that, in the process exemplified in EP-A-0 510 772, the silica acts chemically as a binder for the zirconia particles. In contrast, the filler which may be included in the shapable dough of the present invention remains substantially inert and is present simply to give the dough the appropriate consistency to be shaped. Such a peptizing treatment is not required in the process of the present invention.

It has also been found that the amount of filler required to be added to the zirconia precursor of the present invention prior to shaping is considerably less than the amount of refractory oxide binder that is preferably included in the mixture prior to extrusion in the process described in EP-A-0 510 772. This in turn allows the process of the present invention to be used to prepare shaped zirconia particles having a substantially higher zirconia content than the products of the processes described in the prior art.

After shaping, the preparation of the shaped zirconia precursor preferably comprises a drying stage. Drying may be effected at an elevated temperature, preferably up to about 800° C., more preferably up to about 300° C. The period for drying is typically up to about 5 hours, more preferably from about 30 minutes to about 3 hours.

Calcination of the shaped zirconia precursor will yield shaped zirconia particles. Calcination is effected at an elevated temperature, preferably up to about 1000° C., more preferably from about 200° C. to about 1000° C., most preferably from about 300° C. to about 800° C. Calcination is typically effected for a period of up to 5 hours, preferably from about 30 minutes to about 4 hours. The calcination may be effected, for example, by heating the precursor in air, or by means of direct heating using the hot exhaust gases of a flame to contact the precursor.

The shaped zirconia particles may be used directly as a catalyst. Alternatively, the shaped zirconia particles may be used as a catalyst precursor in the preparation of a final catalyst product.

In use as a catalyst precursor, the shaped zirconia particles are subjected to a deposition stage in which a source of one or more catalytically active components are deposited onto the particles. The source may be of any of the elements in the groups of the Periodic Table of the Elements as discussed hereinbefore. In cases in which the zirconia particles were prepared from a dough comprising a source for a catalytically active component, the deposition of a source for the same or a different element may be effected.

Deposition may be effected by any of the techniques known in the art. A preferred technique for depositing a catalytically active component onto the zirconia particles is impregnation. Impregnation may be effected by contacting the zirconia particles with a compound of the desired element in the presence of a liquid, preferably in the form of a solution of a compound of the element.

A catalytically active component present in the finished catalyst may be present in a total amount of from about 1 to about 100 parts by weight, preferably from about 1 to about 50 parts by weight per hundred parts by weight of carrier.

In a further aspect, the present invention provides a catalyst prepared by a process as hereinbefore described.

The catalyst products of the process of the present invention find use in any process in which a catalyst comprising a catalytically active component, as hereinbefore defined, and a zirconia-containing carrier may be employed. In particular, when the catalytically active component is active as a Fischer-Tropsch catalyst, the catalyst products may be employed in the synthesis of hydrocarbons from a mixture of carbon monoxide and hydrogen, the so-called Fischer-Tropsch synthesis. Typically, the hydrocarbon synthesis reaction is effected at a temperature in the range of from about 125° C. to about 350° C., more preferably from about 175° C. to about 250° C. The reaction pressure is typically in the range of from about 5 bar to about 100 bar, more preferably from about 10 bar to about 50 bar. The hydrogen/carbon monoxide ratio in the feed is typically greater than about 1.5, preferably from about 1.75 to about 2.25, with unconverted carbon monoxide and hydrogen being recycled to contact the catalyst for a second time.

The process of the present invention is further described in the following illustrative examples, which are not intended to be construed as limiting the scope of the present invention and claims. In the examples, the values for the loss on ignition are quoted on the basis of the water lost upon heating the sample to a temperature in the range of from 550° to 600° C.

ILLUSTRATIVE EMBODIMENTS

EXAMPLE 1

Preparation of Zirconia Precursor Gel

A first aqueous solution of ammonium zirconium carbonate was obtained from a commercial supplier (Bacote 20, ex. Magnesium Elektron Limited, 21% wt equivalent of $ZrO_2$, 100 g). A second aqueous solution of zirconium acetate was obtained from a commercial supplier (ex. Magnesium Elektron Limited, 22% wt equivalent of $ZrO_2$, 45 g). The two solutions were mixed together whilst stirring. A rigid gel formed.

Preparation of a Shapable Dough

Sufficient of the gel prepared as described hereinbefore was taken and allowed to dry by evaporation of the water in the gel to give 200 g of a shapable dough. To the shapable dough was added water (5 g) and a flow improver (Nalco) (4 g as a 2% wt aqueous solution). The resulting mixture was mulled for a period of 15 minutes. The resulting shapable dough had a pH of 8.0 and a loss on ignition of 69.6% wt.

Preparation of a Shaped Zirconia Precursor and Catalyst Precursor

The shapable dough prepared as described hereinbefore was extruded using a 1" Bonnot extruder having a 3 mm steel trilobe matrix insert yielding a shaped zirconia precursor in the form of trilobe extrudates having a nominal diameter of 3 mm. The resulting extrudates were dried at a temperature of 120° C. Thereafter, the extrudates were calcined at a temperature of 800° C., yielding a catalyst precursor consisting of white extrudates of zirconia. The catalyst precursor had a reasonable crush strength and a pore volume of 0.1 ml/g.

EXAMPLE 2

Preparation of Zirconia Precursor Gel

A zirconia precursor gel was prepared as described in Example 1 hereabove.

Preparation of a Shapable Dough

The shapable dough thus prepared (290 g), zirconium hydroxide ($Zr(OH)_4$, ex. Magnesium Elektron Limited, 79% wt equivalent of $ZrO_2$, 150 g) and silica (Sipernat 50, ex. Degussa, 34.4% wt equivalent of $SiO_2$, 40 g) were combined and the resulting mixture mulled for 20 minutes to form a shapable dough. A flow improver (Superfloc) (sufficient to give a concentration of about 1% wt on basis of dry dough) was added and the resulting mixture mulled for a further 5 minutes. The resulting mixture was allowed to stand in air under ambient conditions for 24 hours. The resulting shapable dough had a pH of 8.0, a loss on ignition of 49.5% wt and comprised silica in an amount of 16% wt.

Preparation of a Shaped Zirconia Precursor and Catalyst Precursor

The shapable dough prepared as described hereinbefore was extruded using a 1" Bonnot extruder having a 3 mm Delrin trilobe matrix insert yielding a shaped zirconia precursor in the form of trilobe extrudates having a nominal diameter of 3 mm. The resulting extrudates were dried at a temperature of 120° C. Thereafter, the extrudates were calcined at a temperature of 450° C., yielding a catalyst precursor. The physical properties of the catalyst precursor are given in the Table hereinbelow.

TABLE

| | |
|---|---|
| Pore volume | 0.17 ml/g |
| Surface Area | 131 $m^2/g$ |
| Median Pore Diameter | 1320 nm |
| Skeletal Density | 3.15 g/ml |
| Particulate Density | 2.04 g/ml |

Preparation of Catalyst

The catalyst precursor extrudates prepared as described hereinbefore (30 g) was impregnated by contact with a solution of cobalt nitrate ($Co(NO_3)_2.6H_2O$, 11.6 g, prepared as a molten salt by heating to 80° C). The resulting extrudates were dried at a temperature of 120° C. and thereafter calcined by being heated to a temperature of 500° C. over a period of 10 hours and being maintained at that temperature for 1 hour. The resulting catalyst comprised 7.1% wt cobalt, on the basis of the oxidic catalyst.

What is claimed:

1. A process for the preparation of a zirconia precursor, which process comprises contacting and reacting a solution of an acidic zirconium compound with a solution of a basic zirconium compound to form a gel.

2. The process according to claim 1, wherein the acidic zirconium compound is selected from the group consisting of inorganic compounds zirconyl chloride, zirconyl nitrate, zirconium chloride, zirconium phosphate, organic compounds zirconium acetate, zirconium ethanoate and zirconium propanoate, and mixtures thereof.

3. The process according to claim 1, wherein the basic zirconium compound is selected from the group consisting of zirconium carbonate and ammonium zirconium carbonate.

4. The process according to claim 1, wherein a solvent selected from the group consisting of water, an alcohol, a ketone, an aldehyde, an aromatic solvent, and mixtures thereof is used to form each solution.

5. A process for the preparation of a shapable dough suitable for use in the preparation of a shaped zirconia precursor, which process comprises rendering shapable zirconia precursor prepared by a process which comprises contacting and reacting a solution of an acidic zirconium compound with a solution of a basic zirconium compound to form a gel.

6. The process according to claim 5, wherein the shapable dough is obtained by drying said zirconia precursor.

7. The process according to claim 6, wherein the shapable dough is obtained by combining the zirconia precursor with a solid filler.

8. The process according to claim 7, wherein the filler is a refractory oxide selected from the group consisting of alumina, silica, titania, zirconia and mixtures thereof.

9. The process according to claim 5, wherein the shapable dough has a solids content in the range of from about 20% by weight to 60% by weight.

10. The process according to claim 5, wherein the shapable dough is prepared by mulling for a period of from about 10 to about 120 minutes.

11. The process according to claim 5, wherein a flow improver is added during the preparation of the shapable dough in an amount in the range of from about 1% be weight to about 20% by weight, basis the basis of the total weight of the mixture.

12. The process according to claim 5, wherein a source of a catalytically active component is added during the preparation of the shapable dough.

* * * * *